(12) United States Patent
Ishii

(10) Patent No.: US 6,338,666 B1
(45) Date of Patent: Jan. 15, 2002

(54) GIRDLE FOR TREATMENT OF LUMBAGO

(76) Inventor: Shunichirou Ishii, 676, Oaza Sasai, Ogawa-machi, Higashiibaraki-gun, Ibaraki, 311-3402 (JP)

( * ) Notice: Subject to any disclaimer, the term of this patent is extended or adjusted under 35 U.S.C. 154(b) by 0 days.

(21) Appl. No.: 09/807,417

(22) PCT Filed: Dec. 20, 2000

(86) PCT No.: PCT/JP00/09031

§ 371 Date: Aug. 1, 2001

§ 102(e) Date: Aug. 1, 2001

(51) Int. Cl.$^7$ .................................................. A41C 1/08
(52) U.S. Cl. ........................... 450/96; 450/155; 450/97; 450/122
(58) Field of Search ................................ 450/155, 151, 450/96, 94, 97, 98, 100, 101, 115, 126, 116, 127, 122, 123, 131, 128, 132, 125, 133; 128/90.1, 96.1, 101.1, 100.1; 602/19; 2/44, 45, 310–312, 338, 237, 221, 76, 92, 400–408, 227, 228, 220

(56) References Cited

U.S. PATENT DOCUMENTS

| | | | | |
|---|---|---|---|---|
| 1,185,672 A | * | 6/1916 | Huettner | 450/155 |
| 1,572,826 A | * | 2/1926 | Virgen | 450/155 |
| 2,584,279 A | * | 2/1952 | McDowell | 450/155 |
| 3,454,003 A | * | 7/1969 | Kleber-Sailhen | 450/96 |
| 3,524,449 A | * | 8/1970 | Peters | 450/155 |
| 6,080,038 A | * | 6/2000 | Sano | 450/155 |
| 6,146,240 A | * | 11/2000 | Morris | 450/97 |

* cited by examiner

*Primary Examiner*—Gloria M. Hale
(74) *Attorney, Agent, or Firm*—Armstrong, Westerman, Hattori, McLeland and Naughton, LLP

(57) ABSTRACT

According to the present invention, there is provided a lumbago treating girdle comprising: a girdle main body including an inverse-triangular press portion provided with a zipper extending in a vertical direction to a crotch portion from a belt disposed on an upper part of a front surface of the girdle main body, a portion sewn in the vertical direction on a back surface, a right femoral part, a left femoral part, a left engaging member on the left side of the press portion and a right engaging member on the right side of the press portion; a left stretch band which is attached to a middle of a left end portion of the girdle main body, and to a tip end of which a left engaging member with an engaging piece attached to one surface thereof is attached; and a right stretch band which is attached to a middle of a right end portion of the girdle main body, and to a tip end of which a right engaging member with an engaging piece attached to one surface thereof is attached, the left stretch band being attached to the girdle main body in such a manner that the left stretch band ascends toward the left, and the right stretch band being attached to the girdle main body in such a manner that the right stretch band ascends toward the right.

6 Claims, 19 Drawing Sheets

US 6,338,666 B1

GIRDLE FOR TREATMENT OF LUMBAGO

DESCRIPTION

1. Technical Field

The present invention relates to an improvement of a lumbago treating girdle for relieving lumbago and easing one's lumbar.

2. Background Art

There has heretofore been "Body Shaping Girdle" disclosed in Japanese Utility Model Registration Publication No. 2010866 and "Girdle" disclosed in Japanese Patent Application Laid-Open No. 8303/1998.

Additionally, examples of an object fitted with a conventional girdle include adults and children, that is, young and old of both sexes who have lumbago because of functional deterioration and damage of gluteus maximus muscle.

Generally commercial girdles are only standard products having standard sizes such as LMS, and there is no girdle that can finely be adjusted to fit individual body types. Additionally, when a person has to put on the girdle all day long, or walk or act otherwise with the girdle on, the girdle deviates from a fitted position, and the person gains more serious lumbago again.

Moreover, particularly when a fat person with the girdle on sits down, the person's abdomen is doubly pressed by clothing, and girdle only whose abdominal part is adjustable, and the person feels remarkably uneasy and uncomfortable.

Furthermore, a main object of the conventional girdle is to shape the body, and there has been no girdle which is superior in function of treating lumbago in a short term, quickly handling the girdle during urination, or raising one's buttock to provide a beauty effect that one's lower body looks beautiful.

Therefore, an object of the present invention is to provide a lumbago treating girdle which is superior in functions such that one can comfortably have the girdle on without any feeling of pressure, one's body is shaped, comprehensive medicine including prevention, cure, and rehabilitation is possible not only on a substantial lumbago part but also on one's entire lumbar to treat and completely cure the lumbago in a short term, convenience during urination is enhanced, and a beauty effect is produced to make one's lower body look remarkably beautiful.

DISCLOSURE OF THE INVENTION

According to the present invention, there is provided a lumbago treating girdle comprising: a girdle main body including an inverse-triangular press portion provided with a zipper extending in a vertical direction to a crotch portion from a belt disposed on an upper part of a front surface of the girdle main body, a portion sewn in the vertical direction on a back surface, a right femoral part, a left femoral part, a left engaging member on the left side of the press portion and a right engaging member on the right side of the press portion; a left stretch band which is attached to a middle of a left end portion of the girdle main body, and to a tip end of which a left engaging member provided with an engaging piece attached to one surface thereof is attached; and a right stretch band which is attached to a middle of a right end portion of the girdle main body, and to a tip end of which a right engaging member provided with an engaging piece attached to one surface thereof is attached, the left stretch band being attached to the girdle main body in such a manner that the left stretch band ascends toward the left, and the right stretch band being attached to the girdle main body in such a manner that the right stretch band ascends toward the right.

BEST MODE FOR CARRYING OUT THE INVENTION

A girdle for treatment for lumbago according to the present invention will be described in detail with reference to the accompanying drawings.

Figure 1:
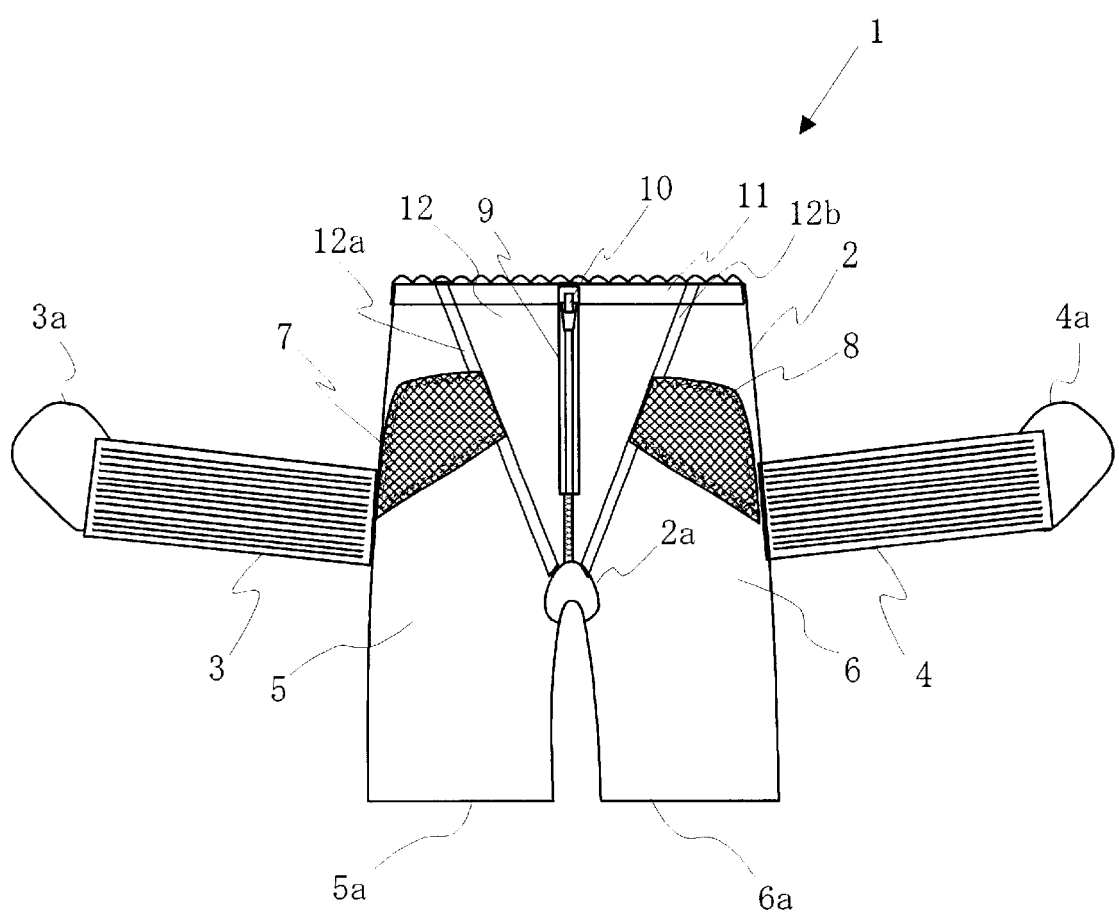
FIG. 1 is a front view showing a first embodiment of a lumbago treating girdle according to the present invention before a stretch band is wound around the lumbago treating girdle.
Figure 2:
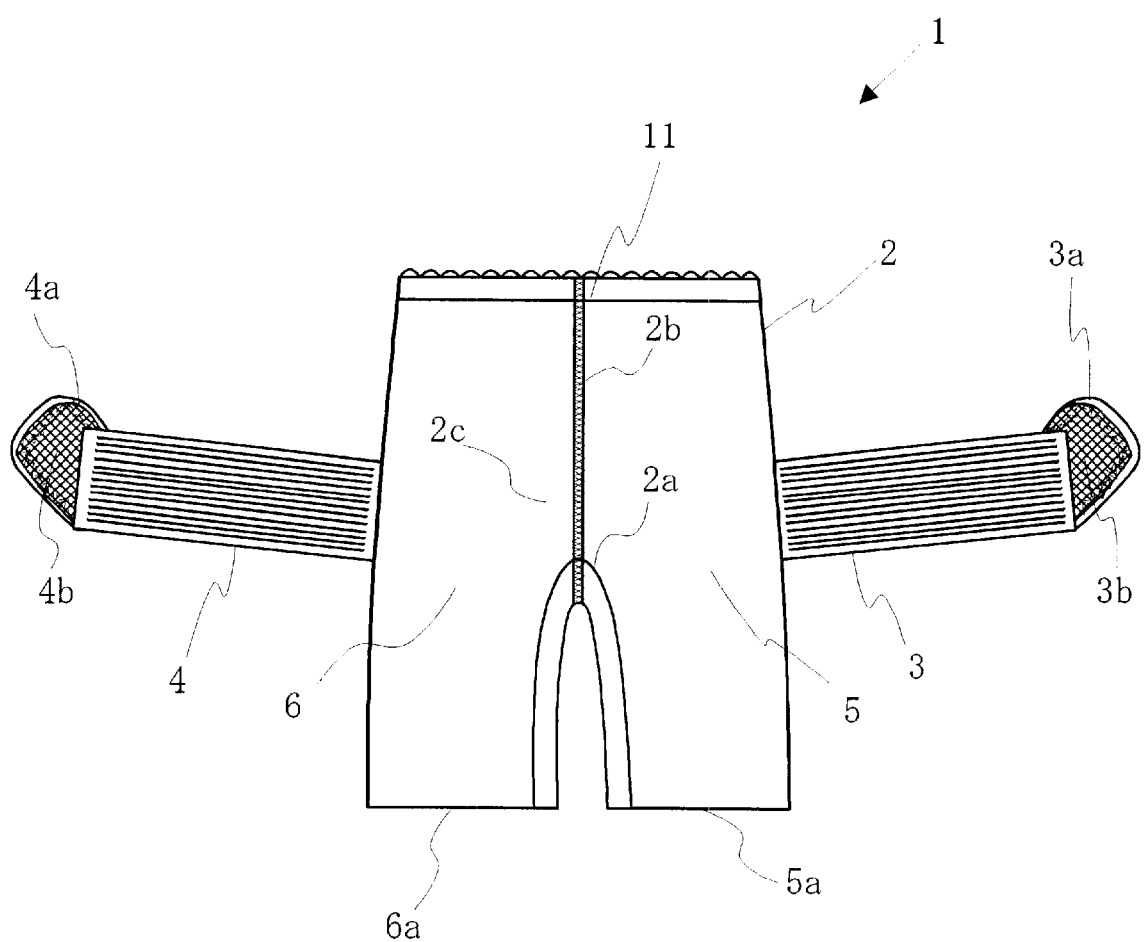
FIG. 2 is a back view showing the first embodiment of the lumbago treating girdle according to the present invention before the stretch band is wound therearound.
Figure 3:
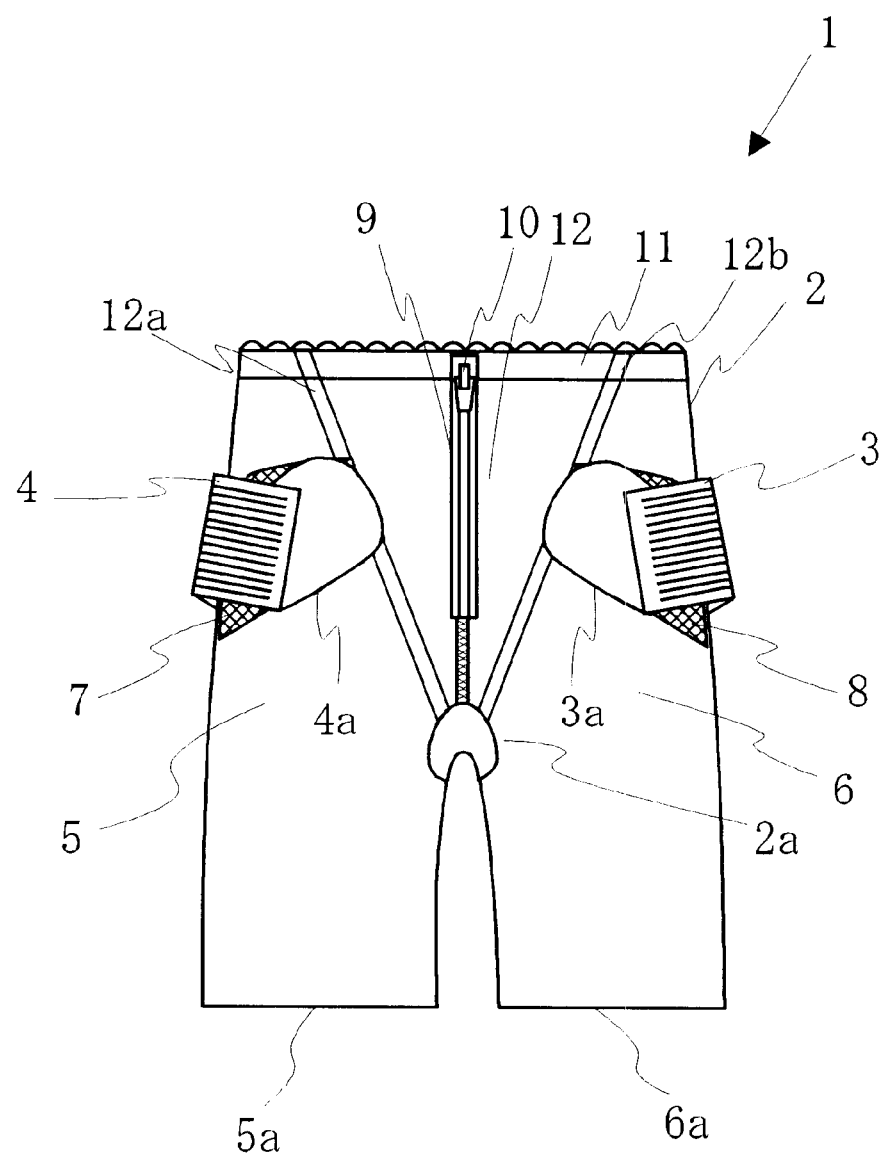
FIG. 3 is a front view showing the first embodiment of the lumbago treating girdle according to the present invention after the stretch band is wound therearound.
Figure 4:
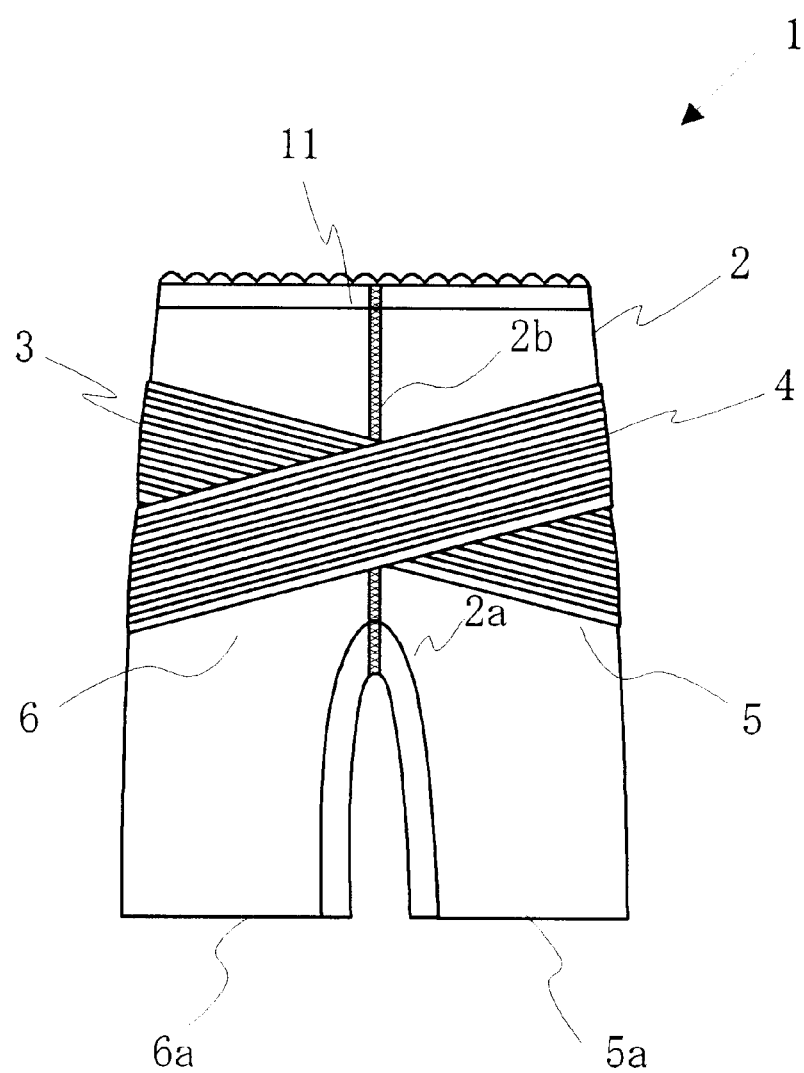
FIG. 4 is a back view showing the first embodiment of the lumbago treating girdle according to the present invention after the stretch band is wound therearound.

FIGS. 1 to 4 are views showing a first embodiment of the lumbago treating girdle of the present invention. FIG. 1 is a front view showing the first embodiment of the lumbago treating girdle according to the present invention before a stretch band is wound around the lumbago treating girdle, FIG. 2 is a back view of the lumbago treating girdle before the stretch band is wound therearound, FIG. 3 is a front view of the lumbago treating girdle after the stretch band is wound therearound, and FIG. 4 is a back view of the lumbago treating girdle after the stretch band is wound therearound.

As shown in FIG. 1, a lumbago treating girdle 1 of the present invention is constituted of: a girdle main body 2 having a right femoral part 5 in which a right leg passing port 5a for passing one's right-leg right femoral part is formed, and a left femoral part 6 in which a left leg passing port 6a for passing one's left-leg left femoral part is formed; and left and right stretch bands 3, 4 attached to left and right end portions of the girdle main body 2.

A material of the left and right stretch bands 3, 4 is, for example, an expandable/contractible material, such as rubber. Particularly, a meshed material superior in air permeability may be used for summer. Moreover, the expandable/contractible material is preferably used for winter. In this manner, the material can selectively be used in accordance with functions suitable for seasons.

A belt 11 is formed in an upper part of the girdle main body 2, and an entirely inverse triangular press portion 12 is formed to extend from the band 11 to a crotch portion 2a in a front surface of the girdle main body 2. In the inverse triangular press portion 12, a thick core is inserted, and surrounded with left and right seams 12a, 12b.

Left and right engaging members 3a, 4a are sewn and attached to tip ends of the left and right stretch bands 3, 4, or integrally formed on the tip ends of the left and right stretch bands 3, 4. Lower ends of the left and right seams 12a, 12b are connected to the crotch portion 2a.

As shown in FIG. 1, the belt 11 provided with a plurality of semicircular trimmings is attached to the upper part of the girdle main body 2, and a zipper 9 is attached to a middle portion of the inverse triangular press portion 12 in a vertical direction. Reference numeral 10 denotes an opening/closing metal piece for opening/closing the zipper 9.

Moreover, a left engaging member 7 formed substantially in a trapezoidal shape is attached to the left side of the left seam 12a of the press portion 12, and a right engaging member 8 is attached to the right side of the right seam 12b of the press portion 12. The stretch band 3 is attached substantially to a middle of a left end of the girdle main body 2, and the engaging member 3a formed substantially in a semicircular shape is attached to the tip end of the stretch band in such a manner that a left end of the engaging member 3a is tilted upward to the left. An engaging piece 3b is attached to a back surface of the engaging member 3a. The engaging piece 3b is attached only to the back surface.

Moreover, the stretch band 4 is attached substantially to a right end of the girdle main body 2, and the engaging member 4a formed substantially in the semicircular shape is attached to the tip end of the stretch band in such a manner that a right end of the engaging member 4a is tilted upward to the right. An engaging piece 4b is attached to the back surface of the engaging member 4a. Respective tip ends of the engaging members 3a, 4a are formed in circular shapes, and the engaging piece 4b is attached only to the back surface. The engaging members 3a, 4a are attached to the tip ends of the left and right stretch bands 3, 4 in such a manner that the respective tip ends of the engaging members are tilted upward to the left and right, that is, obliquely turn to an upward direction.

FIG. 2 is a back view showing the first embodiment of the lumbago treating girdle according to the present invention before the stretch band is wound around girdle. As shown in FIG. 2, the left stretch band 3 is attached to the girdle main body 2 in such a manner that the tip end of the left stretch band 3 ascends toward the left. Moreover, the right stretch band 4 is attached to the girdle main body 2 in such a manner that the tip end of the right stretch band 4 slightly ascends toward the right. No press portion 12 is disposed in the back surface of the girdle main body 2, and a sewn portion 2b is disposed in the middle of the back surface to vertically extend downward to the crotch portion 2a from the belt 11 disposed in the upper part of the girdle main body 2.

Moreover, FIG. 3 is a front view showing the first embodiment of the lumbago treating girdle according to the present invention after the stretch band is wound around the girdle.

As shown in FIG. 3, the engaging piece 3b attached to the engaging member 3a attached to the tip end of the left stretch band 3 is joined to the left engaging member 7, and the engaging piece 4b attached to the right engaging member 4a is joined to the right engaging member 8. FIG. 4 is a back view showing the first embodiment of the lumbago treating girdle according to the present invention after the stretch band is wound around the girdle. The left and right stretch bands 3, 4 attached to the girdle main body 2 are crossed in an X shape and wound around the vicinity of the center of a buttock portion 2c of the back surface during use.

As shown in FIGS. 3, 4, when the engaging pieces 3b, 4b of the left and right engaging members 3a, 4a attached to the tip ends of the left and right stretch bands 3, 4 are joined to the left and right engaging members 7, 8 in slightly deviating positions, intensity of feeling of fitting of the stretch bands 3, 4 can be adjusted.

When a fat person puts on the present lumbago treating girdle 1 and sits, the person's abdomen is pressed by the press portion 12 sewn onto the front surface of the girdle main body 2 with the seams 12a, 12b shown in FIG. 3. In this case, the press portion 12 spreads forward with the seams 12a, 12b for fine adjustment so that the person's abdomen is prevented from being pressed.

Figure 5:
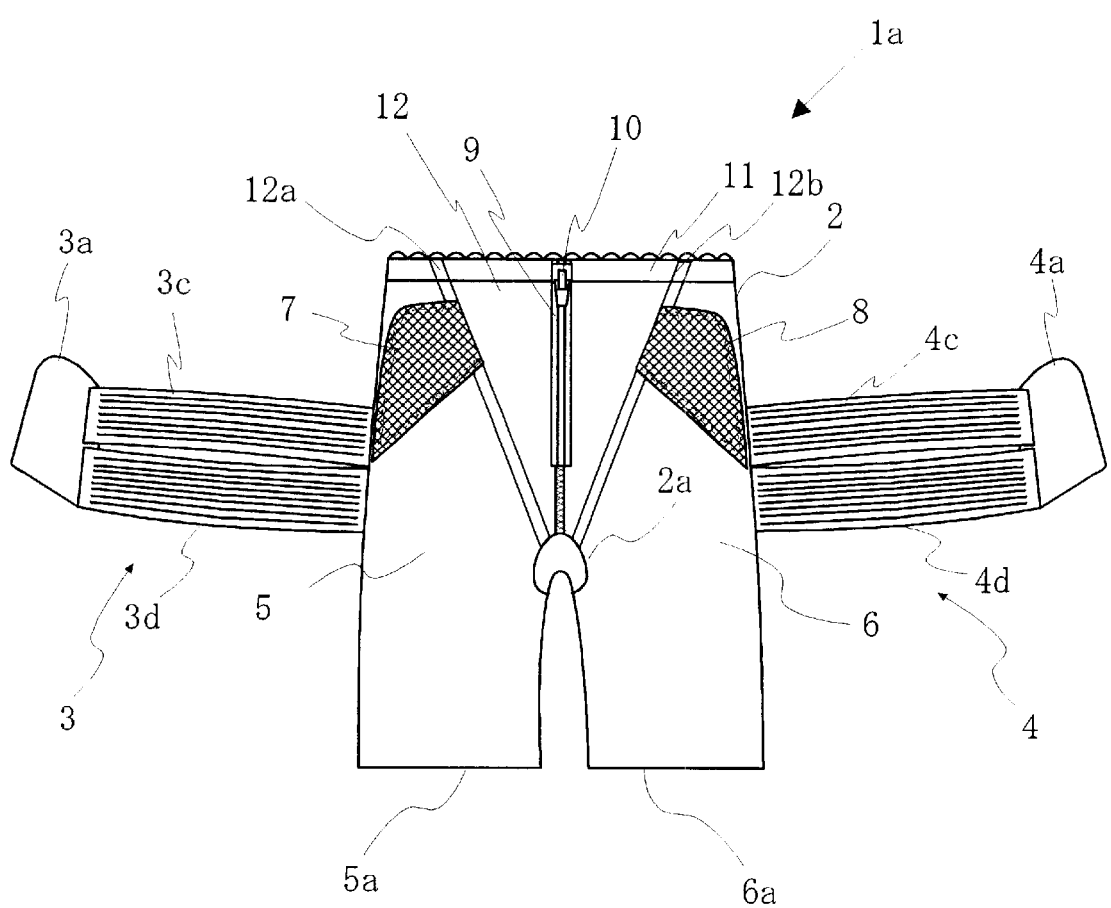
FIG. 5 is a front view showing a second embodiment of the lumbago treating girdle according to the present invention before the stretch band is wound therearound.
Figure 6:
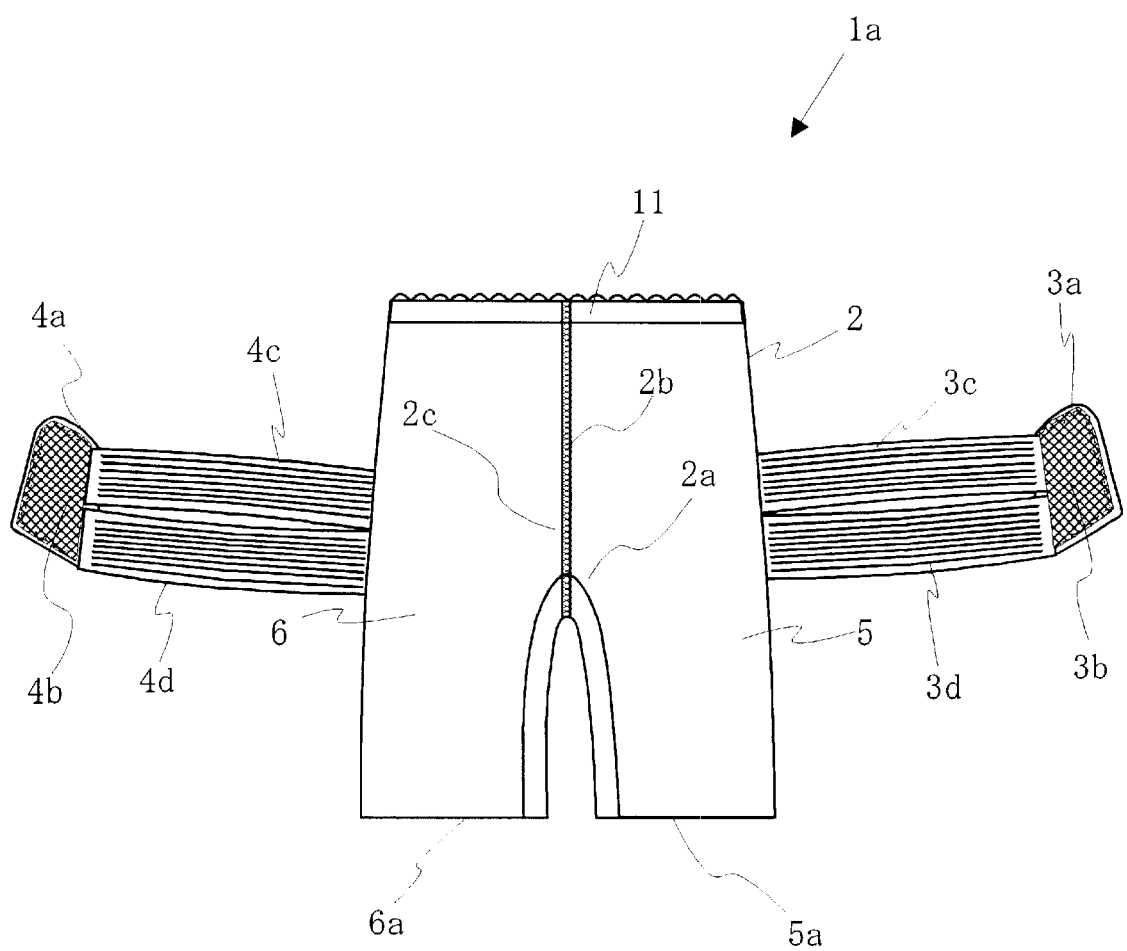
FIG. 6 is a back view showing the second embodiment of the lumbago treating girdle according to the present invention before the stretch band is wound therearound.
Figure 7:
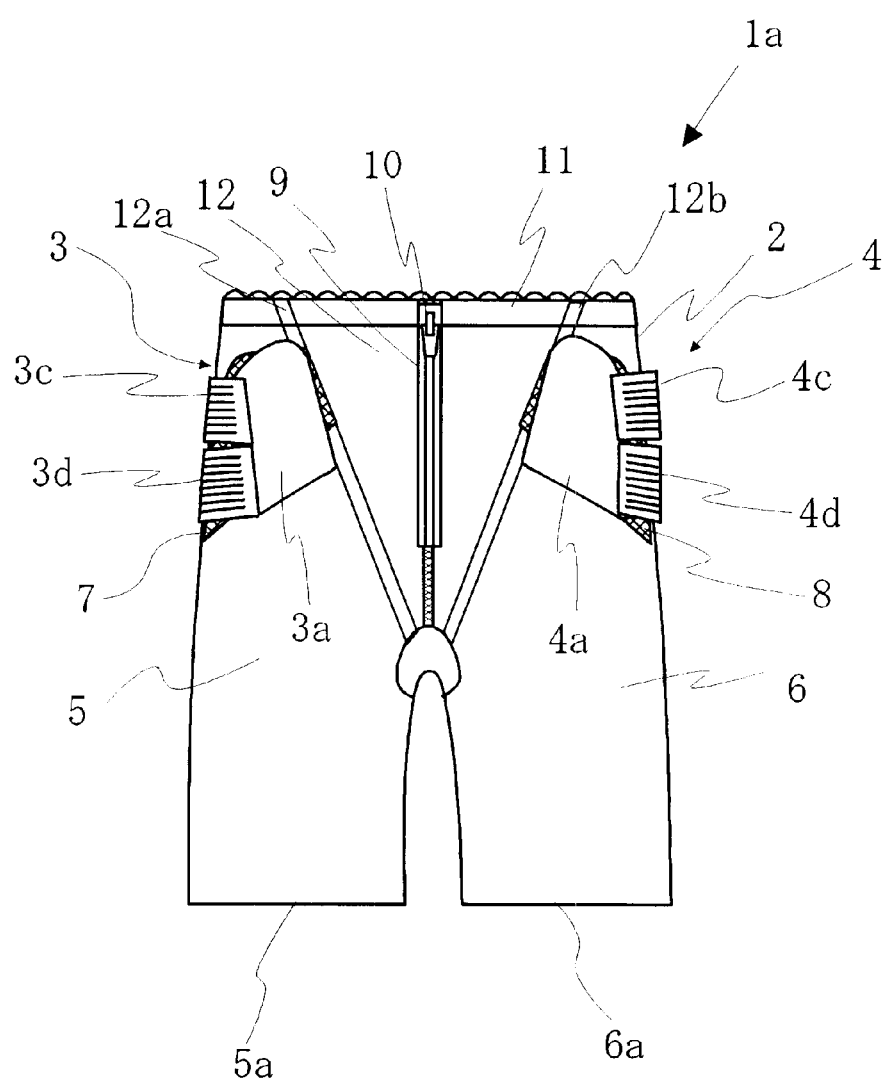
FIG. 7 is a front view showing the second embodiment of the lumbago treating girdle according to the present invention after the stretch band is wound therearound.
Figure 8:
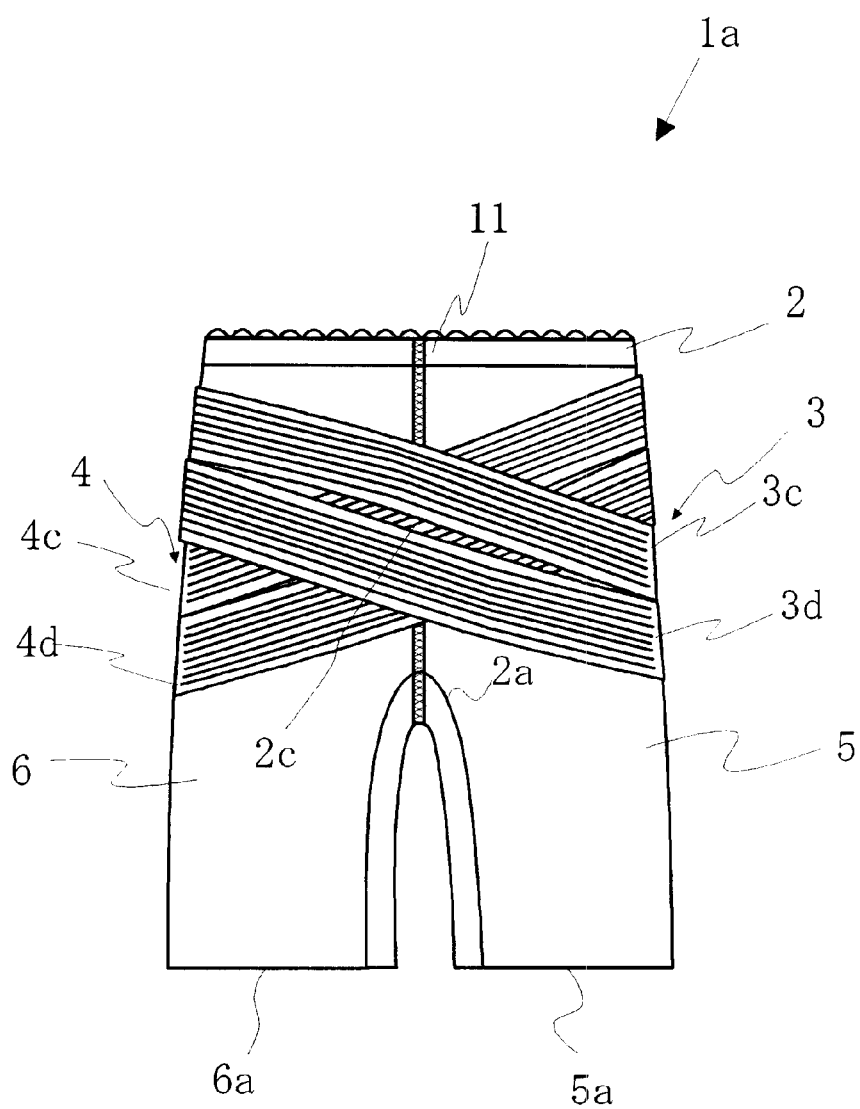
FIG. 8 is a back view showing the second embodiment of the lumbago treating girdle according to the present invention after the stretch band is wound therearound.

FIG. 5 to 8 show a second embodiment of the lumbago treating girdle of the present invention. FIG. 5 is a front view showing the second embodiment of the lumbago treating girdle according to the present invention before the stretch band is wound around the girdle, FIG. 6 is a back view showing the second embodiment of the lumbago treating girdle according to the present invention before the stretch band is wound around the girdle, FIG. 7 is a front view showing the second embodiment of the lumbago treating girdle according to the present invention after the stretch band is wound around the girdle, and FIG. 8 is a back view showing the second embodiment of the lumbago treating girdle according to the present invention after the stretch band is wound around the girdle.

A lumbago treating girdle 1a of the second embodiment is largely different from the lumbago treating girdle 1 of the first embodiment in that the left or right engaging member 3a, 4a with the left or right engaging piece 3b, 3c attached to the back surface thereof is attached to tip ends of two left or right stretch bands 3, 4, instead of one left or right stretch band 3, 4.

That is to say, as shown in FIG. 5, left upper and lower stretch bands 3c, 3d are attached to the left end of the girdle main body 2 in such a manner that the tip ends of the bands slightly ascend toward the left. The left engaging member 3a with the engaging piece 3b attached to the back surface thereof is sewn and attached to the tip ends of the left upper and lower stretch bands 3c, 3d in such a manner that the tip end of the member slightly ascends toward the left.

Moreover, right upper and lower stretch bands 4c, 4d are attached to the right end of the girdle main body 2 in such a manner that the tip ends of the bands slightly ascend toward the right. The right engaging member 4a with the engaging piece 4b attached to the back surface thereof is sewn and attached to the tip ends of the right upper and lower stretch bands 4c, 4d in such a manner that the tip end of the member slightly ascends toward the right.

The other constitution of the lumbago treating girdle 1a of the second embodiment is the same as that of the lumbago treating girdle 1 of the first embodiment.

As shown in FIGS. 5 to 8, since the right or left stretch band is formed of two upper and lower stretch bands 3c and 3d, or 4c and 4d, one's buttock can securely be pressed, pelvis is stabilized, and lumbago can be prevented.

In the lumbago treating girdle 1a of the second embodiment, each of the left and right stretch bands 3, 4 is formed of two bands, but may be formed of three, or four bands, if necessary.

Figure 9:
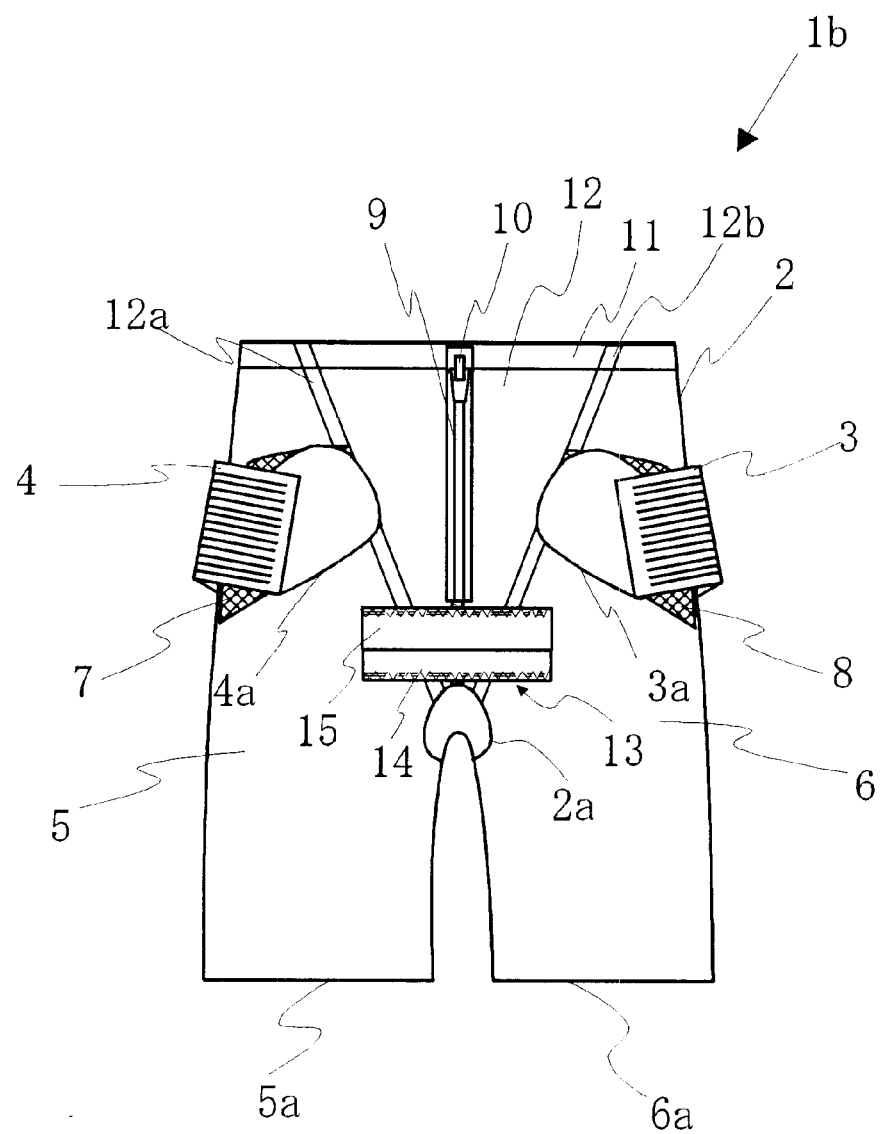
FIG. 9 is a front view showing a third embodiment of the lumbago treating girdle according to the present invention after the stretch band is wound therearound.

FIG. 9 is a front view showing a third embodiment of the lumbago treating girdle according to the present invention after the stretch band is wound around the girdle.

A lumbago treating girdle 1b of the third embodiment is constituted by disposing an opening/closing portion 13 above the crotch portion 2a on the front surface of the girdle main body 2 of the lumbago treating girdle 1 described in the first embodiment. Moreover, the other constitution is the same as that of the lumbago treating girdle 1 of the first embodiment.

As shown in FIG. 9, since the opening/closing portion 13 is disposed right above the crotch portion 2a in the middle part of the girdle main body 2, this structure is convenient for a man with the lumbago treating girdle 1b thereon during urination.

Figure 10:
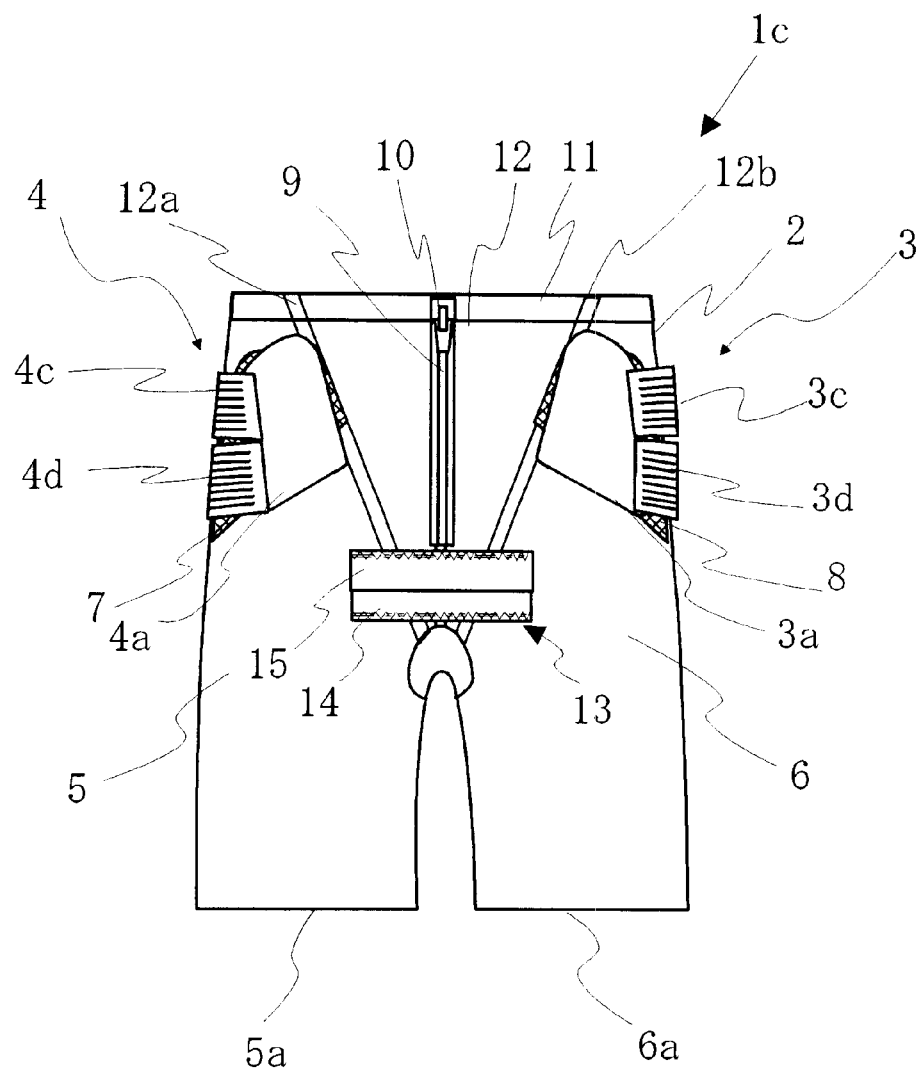
FIG. 10 is a front view showing a fourth embodiment of the lumbago treating girdle according to the present invention after the stretch band is wound therearound.

FIG. 10 is a front view showing a fourth embodiment of the lumbago treating girdle according to the present invention after the stretch band is wound around the girdle. A lumbago treating girdle 1c of the fourth embodiment is constituted by disposing the opening/closing portion 13 above the crotch portion 2a on the front surface of the girdle main body 2 of the lumbago treating girdle 1a described in the second embodiment. Moreover, the other constitution is the same as that of the lumbago treating girdle 1a of the second embodiment.

Figure 11:
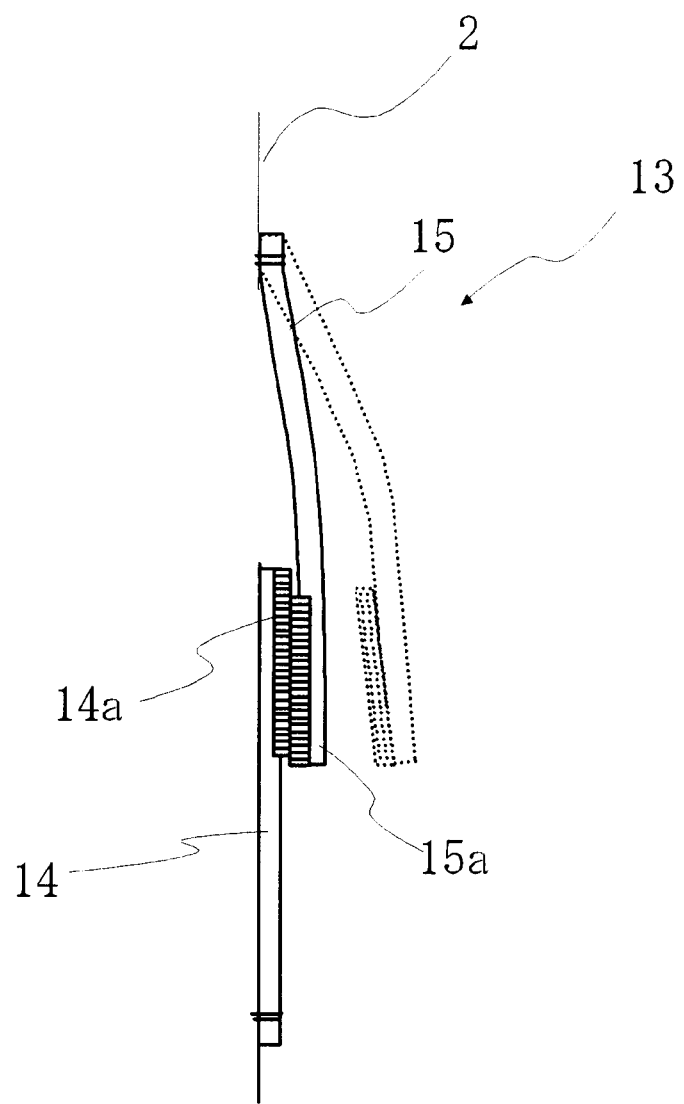
FIG. 11 is a longitudinal sectional view of an opening/closing portion disposed in the third and fourth embodiments of the lumbago treating girdle according to the present invention.

As shown in FIG. 10, the opening/closing portion 13 is disposed right above the crotch portion 2a in the middle part of the girdle main body 2. Therefore, when a man puts on the lumbago treating girdle 1c, urination is facilitated. FIG. 11 is a longitudinal sectional view of the opening/closing portion disposed in the third and fourth embodiments of the lumbago treating girdle according to the present invention, and FIG. 12 is a longitudinal sectional view of another example of the opening/closing portion disposed in the third and fourth embodiments of the lumbago treating girdle according to the present invention.

As shown in FIG. 11, the opening/closing portion 13 is constituted of a lower opening/closing piece 14 and an upper opening/closing piece 15 attached to the girdle main body 2. An engaging portion 14a is attached to an outer surface of the lower opening/closing piece 14, and an engaging portion 15a is attached to an inner surface of a lower end of the upper opening/closing piece 15. In the opening/closing portion 13, the upper opening/closing piece 15 is positioned outside the lower opening/closing piece 14.

Figure 12:
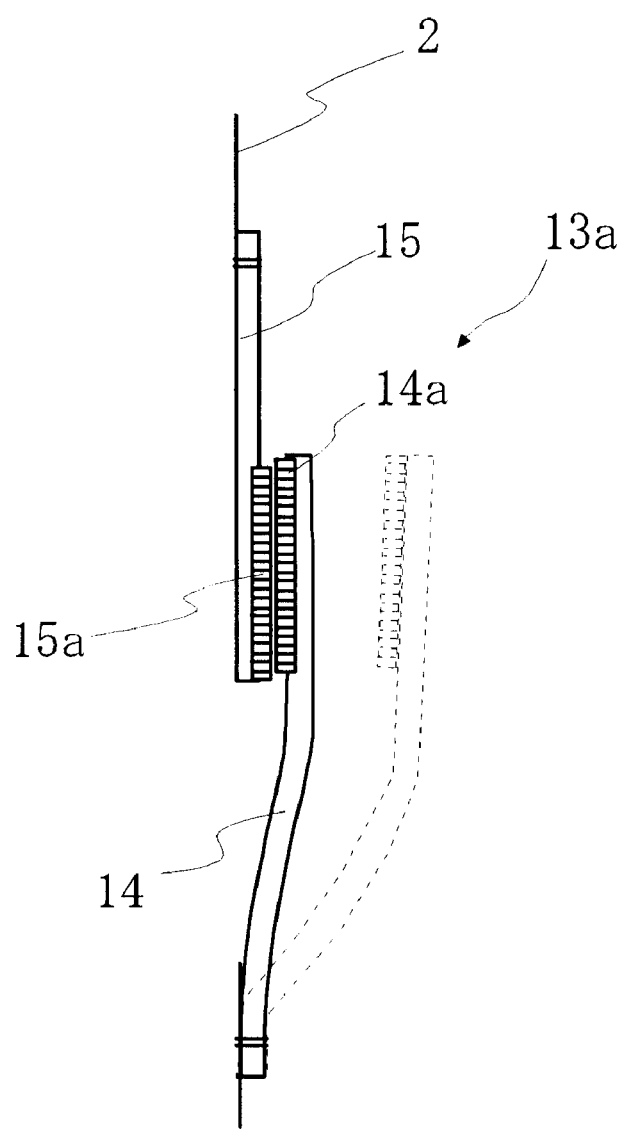
FIG. 12 is a longitudinal sectional view of another example of the opening/closing portion disposed in the third and fourth embodiments of the lumbago treating girdle according to the present invention.

An opening/closing portion 13a shown in FIG. 12 is different in structure from the opening/closing portion 13 shown in FIG. 11. That is to say, in the opening/closing portion 13a of the present example, the engaging portion 14a is attached to the inner surface of the upper end of the lower opening/closing piece 14, and the engaging portion 15a is attached to the outer surface of the lower end of the upper opening/closing piece 15. Moreover, the lower end of the upper opening/closing piece 15 is positioned inside, the upper end of the lower opening/closing piece 14 is positioned outside, and the engaging portion 15a of the upper opening/closing piece 15 engages with the engaging portion 14a of the lower opening/closing piece 14. The engaging portion 14a of the lower opening/closing piece 14 is detachably attached to the engaging portion 15a of the upper opening/closing piece 15.

Figure 13:
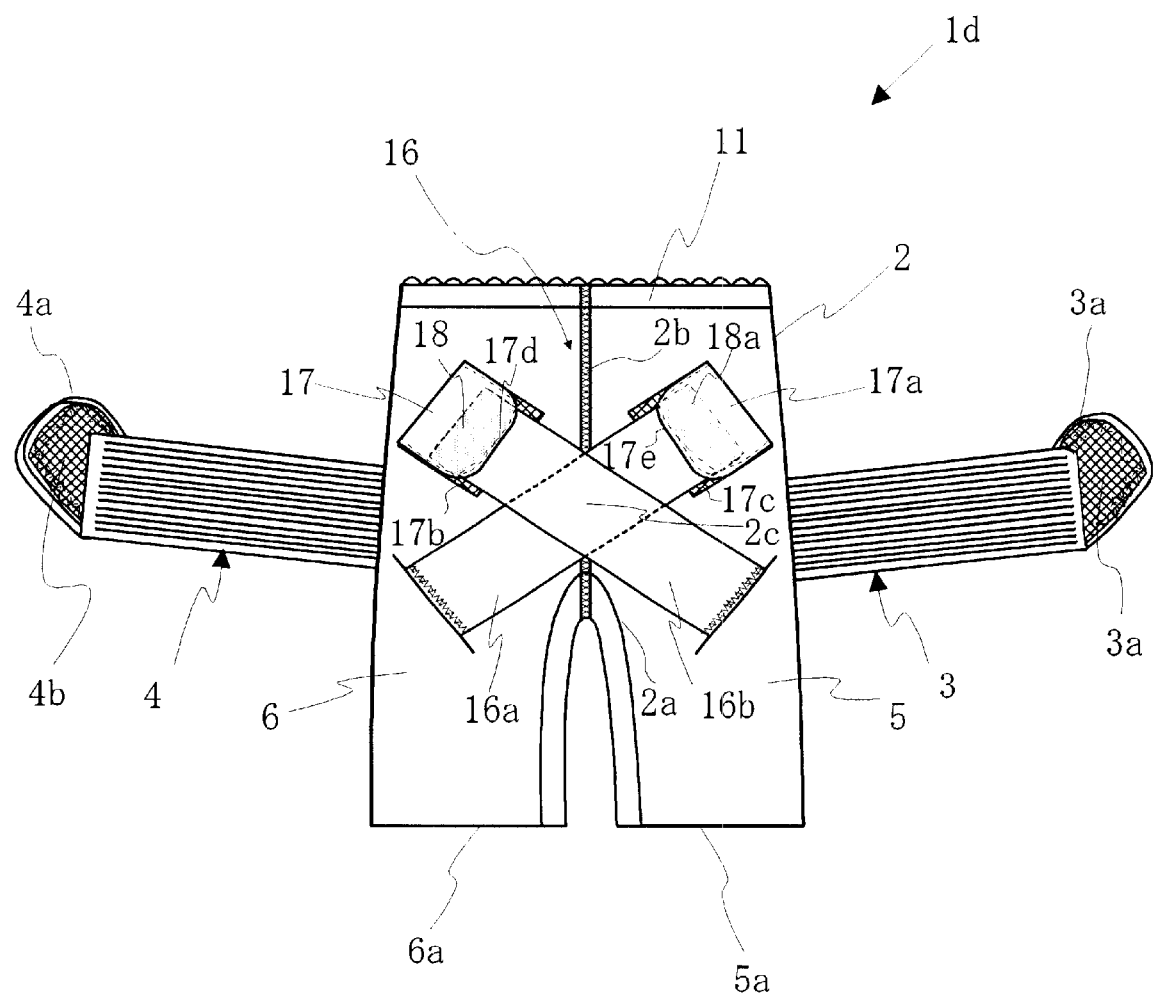
FIG. 13 is a back view showing a fifth embodiment of the lumbago treating girdle according to the present invention before the stretch band is wound therearound.

FIG. 13 is a back view showing a fifth embodiment of the lumbago treating girdle according to the present invention before the stretch band is wound around the girdle. A lumbago treating girdle id of the fifth embodiment is constituted by disposing a cross band portion 16 on the back surface of the girdle main body 2 of the lumbago treating girdle 1 of the first embodiment shown in FIGS. 1 to 4.

As shown in FIG. 13, in the lumbago treating girdle 1d of the fifth embodiment, the cross band portion 16 is constituted of: a left cross band 16a whose one end is sewn to the left femoral part 6 of the girdle main body 2; a right cross band 16b whose one end is sewn to the right femoral part 5 of the girdle main body 2; and left and right engaging members 17, 17a for engaging with the other ends of the left and right cross bands 16a, 16b.

For the left cross band 16a, one end of the left cross band 16a is sewn to the left femoral part 6 so as to ascend toward the right, and one end of the right cross band 16b is sewn to the right femoral part 5 so as to ascend toward the left. Moreover, the left and right engaging members 17, 17a are attached to predetermined positions of the upper part of the back surface of the girdle main body 2, with which the tip ends of the left and right cross bands 16a, 16b can engage. When the tip end of the left cross band 16a is joined to the right engaging member 17a and the tip end of the right cross band 16b is joined to the left engaging member 17 in a wrapped manner, the left and right cross bands 16a, 16b cross each other in an X shape.

Figure 14:
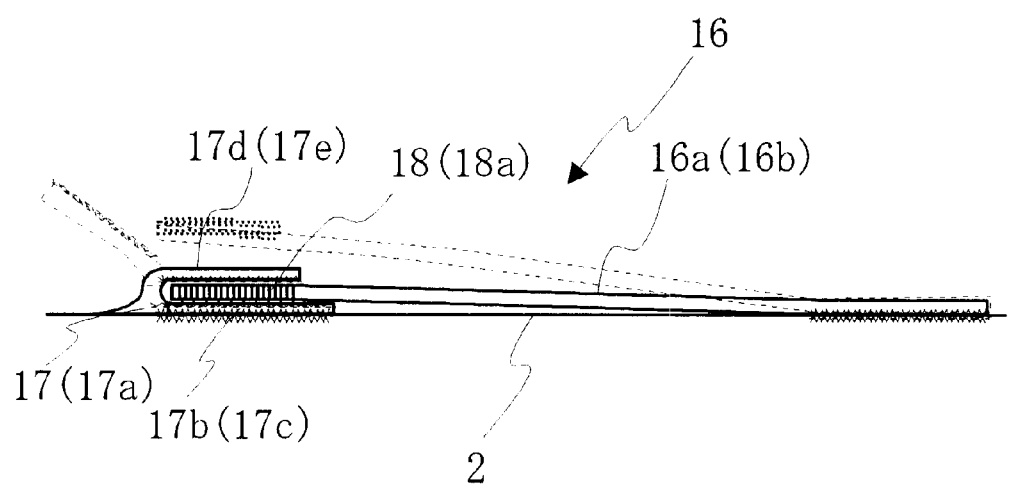
FIG. 14 is a longitudinal sectional view of a cross band of the fifth embodiment of the lumbago treating girdle according to the present invention.

FIG. 14 is a longitudinal sectional view of the cross band of the fifth embodiment of the lumbago treating girdle according to the present invention. As shown in FIG. 14, one end of the left or right cross band 16a, 16b is sewn to the back surface of the girdle main body 2, and the other end (tip end) thereof is provided with an engaging portion 18, 18a.

On the back surface of the girdle main body 2, the left and right engaging members 17, 17a attached to the positions with which the tip ends of the left and right cross bands 16a, 16b can engage have U-shaped sectional shapes, and lower engaging pieces 17b, 17c constituting the U-shaped left and right engaging members 17, 17a are sewn to the back surface of the girdle main body 2. On the inner surfaces of upper engaging pieces 17d, 17e and the upper surface of the lower engaging pieces 17b, 17e constituting the left and right engaging members 17, 17a, engaging portions for engaging with the engaging portions 18, 18a attached to the tip ends of the left and right cross bands 16a, 16b are attached.

In FIG. 14, as shown by dotted lines, the upper engaging pieces 17d, 17e can be raised/lowered. In this manner, the tip ends of the left and right cross bands 16, 16b can be held and joined into the U-shaped left and right engaging members 17, 17a in the wrapped manner. The cross band portion 16 may be attached to the back surface of the girdle main body 2 of the lumbago treating girdle 1a of the second embodiment according to the present invention.

Figure 15:
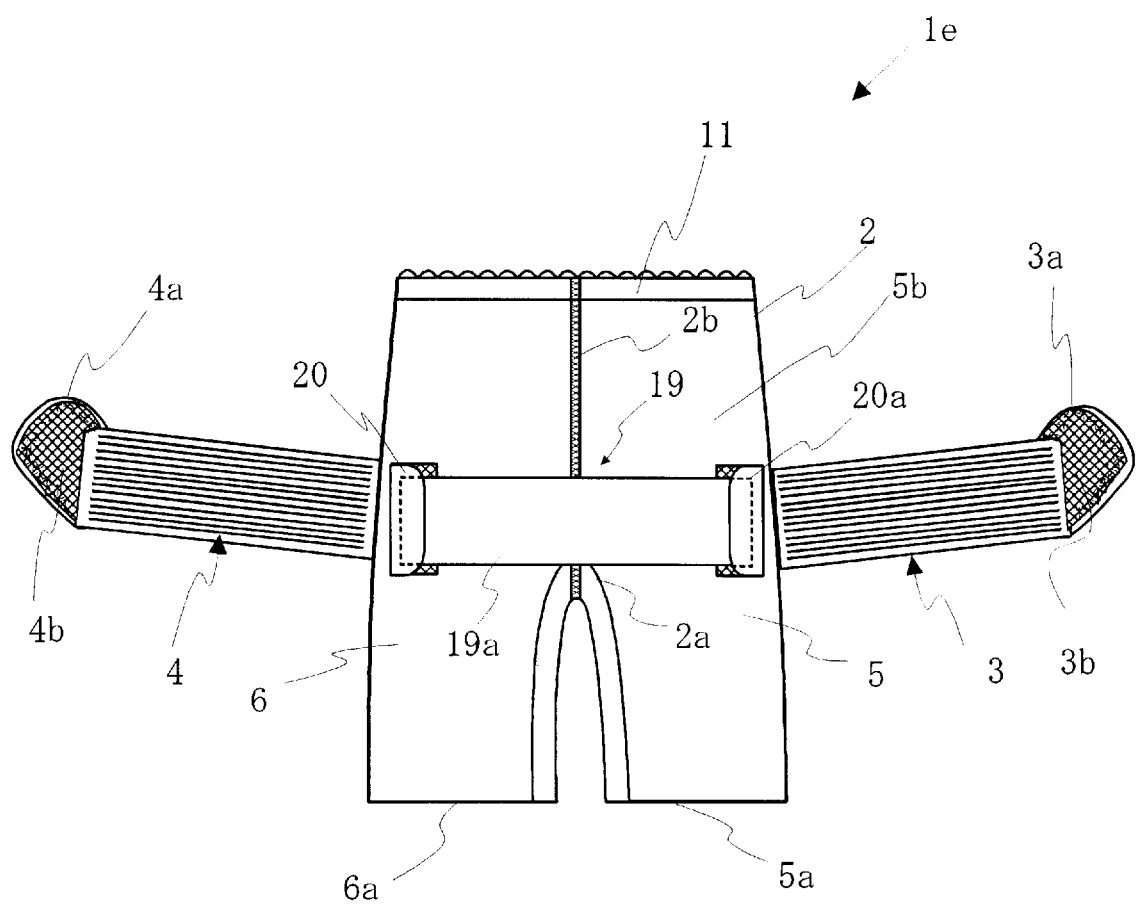
FIG. 15 is a back view showing a sixth embodiment of the lumbago treating girdle according to the present invention before the stretch band is wound therearound.
Figure 16:
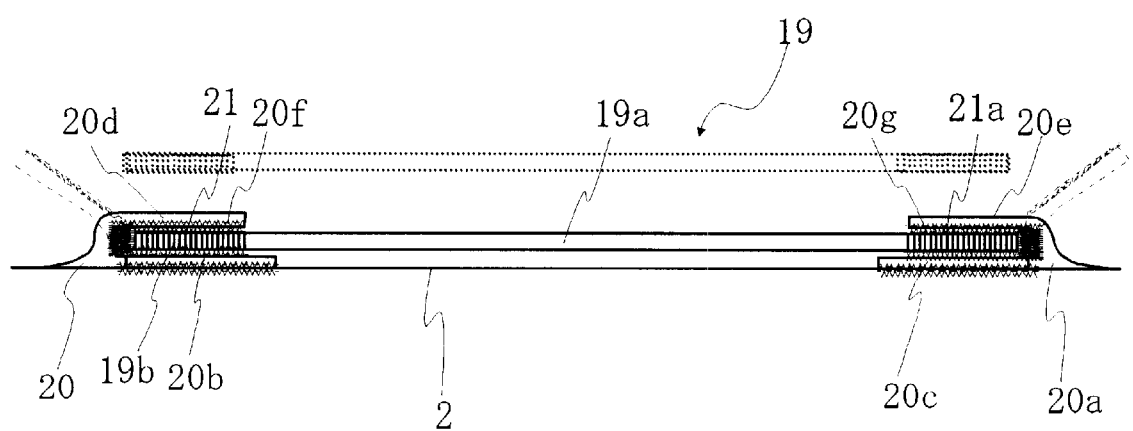
FIG. 16 is a longitudinal sectional view of a horizontal band of the sixth embodiment of the lumbago treating girdle according to the present invention.
Figure 17:
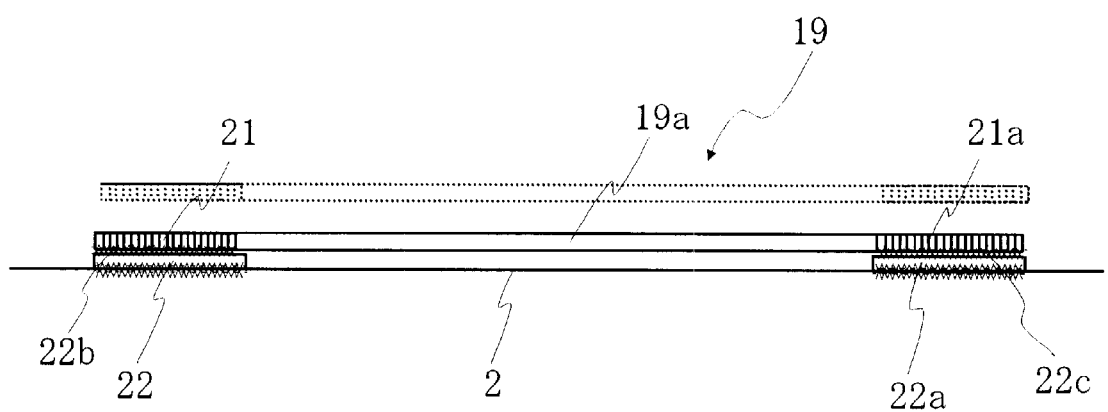
FIG. 17 is a longitudinal sectional view of another example of the horizontal band disposed in the sixth embodiment of the lumbago treating girdle according to the present invention.

FIGS. 15 to 17 show a sixth embodiment of the lumbago treating girdle according to the present invention. FIG. 15 is a back view showing the sixth embodiment of the lumbago treating girdle according to the present invention before the stretch band is wound around the girdle, FIG. 16 is a longitudinal sectional view of a horizontal band of the sixth embodiment of the lumbago treating girdle according to the present invention, and FIG. 17 is a longitudinal sectional view of another example of the horizontal band disposed in the sixth embodiment of the lumbago treating girdle according to the present invention.

As shown in FIG. 15, a lumbago treating girdle 1e of the sixth embodiment is a lumbago treating girdle in which a horizontal band portion 19 is disposed on the back surface of the girdle main body 2 of the lumbago treating girdle 1 according to the first embodiment shown in FIGS. 1 to 4. For the lumbago treating girdle 1e of the sixth embodiment, as shown in FIG. 15, the horizontal band portion 19 is constituted of: a horizontal band 19a with engaging portions 21, 21a attached to left and right end portions thereof; and left and right engaging members 20, 20a, attached to left and right positions of substantially the middle part of the back surface of the girdle main body 2, for engaging with the horizontal band 19a.

The left and right engaging members 20, 20a are attached to the back surface of the horizontal band 19a of the horizontal band portion 19 such that the engaging members are substantially linearly aligned with the left and right stretch bands 3, 4.

As shown in FIG. 16, the left and right engaging members 20, 20a of the horizontal band portion 19 attached to the middle part of the back surface of the girdle main body 2 have a U-shaped longitudinal section, and upper engaging pieces 20d, 20e are connected to lower engaging pieces 20b, 20c.

Engaging portions 20f, 20g are attached to between the upper engaging pieces 20d, 20e and the lower engaging pieces 20b, 20c of the left and right engaging members 20, 20a, and engaging portions 19b, 19c attached to left and right ends of the horizontal band 19a engage with the engaging portions 20f, 20g, so that the horizontal band 19a can be detachably attached to between the left and right engaging members 20 and 20a.

As shown in FIG. 17, instead of the U-shaped left and right engaging members 22, 22a, flat left and right engaging members 22, 22a are attached to the back surface of the girdle main body 2, and engaging portions 22b, 22c may be attached to upper surfaces of the engaging members. The horizontal band 19a is detachably attached to between the left and right engaging members 22 and 22a. In FIG. 15, one stretch band 3, 4 with the engaging member 3a, 4a sewn thereto is disposed on either one side, but instead of one horizontal band 19a, a plurality of horizontal bands may be detachably attached to the horizontal band portion 19.

Figure 18:
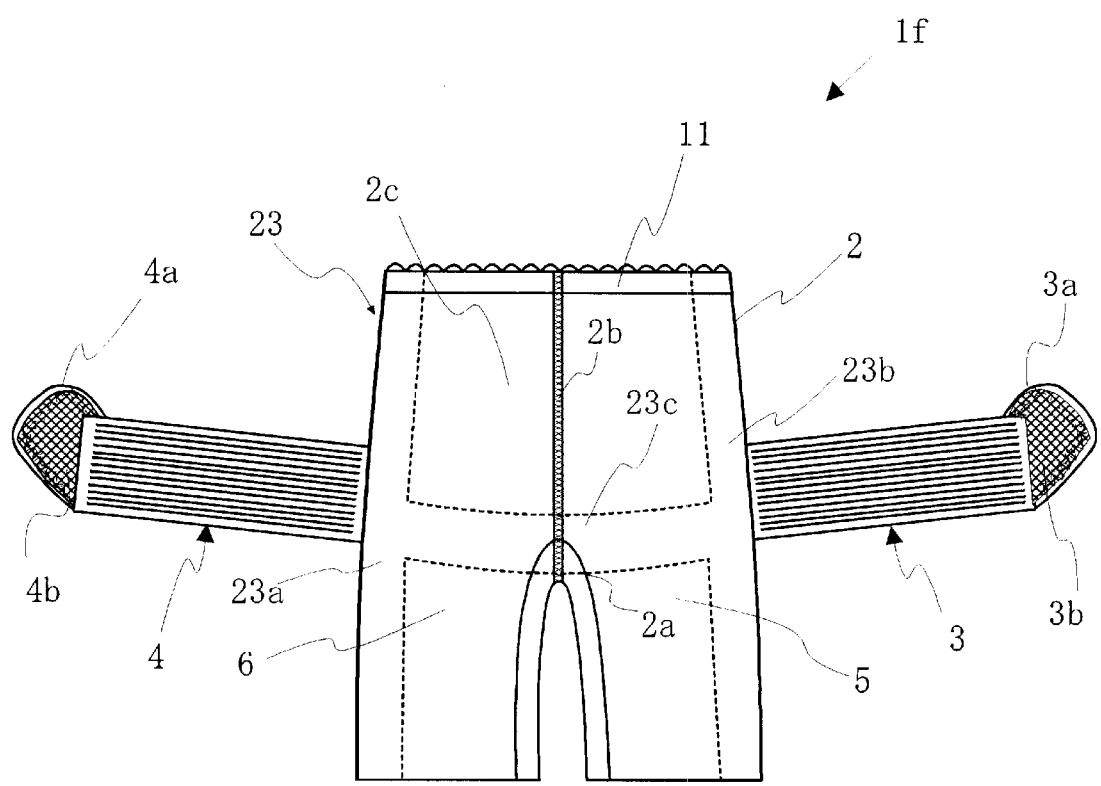
FIG. 18 is a back view showing a seventh embodiment of the lumbago treating girdle according to the present invention before the stretch band is wound therearound.

FIG. 18 is a back view showing a seventh embodiment of the lumbago treating girdle according to the present invention before the stretch band is wound around the girdle. As shown in FIG. 18, in a lumbago treating girdle if of the seventh embodiment, an H-shaped shaping member 23 is sewn onto a back inner surface of the girdle main body 2.

The lumbago treating girdle if of the seventh embodiment is constituted by sewing the H-shaped shaping member 23 onto the back inner surface of the girdle main body 2 of the lumbago treating girdle 1 of the first embodiment. Of course, the H-shaped shaping member 23 may be sewn onto a back outer surface of the girdle main body 2. The shaping member 23 is constituted of a left vertical piece 23a, right vertical piece 23b and horizontal piece 23c. The horizontal piece 23c is disposed substantially in a middle between the left and right vertical pieces 23a and 23b.

In order to sew the shaping member 23 onto the back inner surface of the girdle main body 2, the left vertical piece 23a of the shaping member 23 is sewn onto the left end of the inner surface of the girdle main body 2, the right vertical piece 23b is sewn onto the right end of the inner surface of the girdle main body 2, and the horizontal piece 23c is sewn substantially onto the inner surface of the crotch portion 2a. The H-shaped shaping member 23 is sewn onto the back inner surface of the girdle main body in this manner. Therefore, when one puts on the lumbago treating girdle If of the seventh embodiment, one's lumbar, buttock, femur, and the like can be shaped. The H-shaped shaping member 23 is sewn onto the inner surface. Therefore, even when one puts on the girdle, appearance is good, and one's lower body can look beautiful. It can be expected that especially women like to use this type of lumbago treating girdle.

Figure 19:
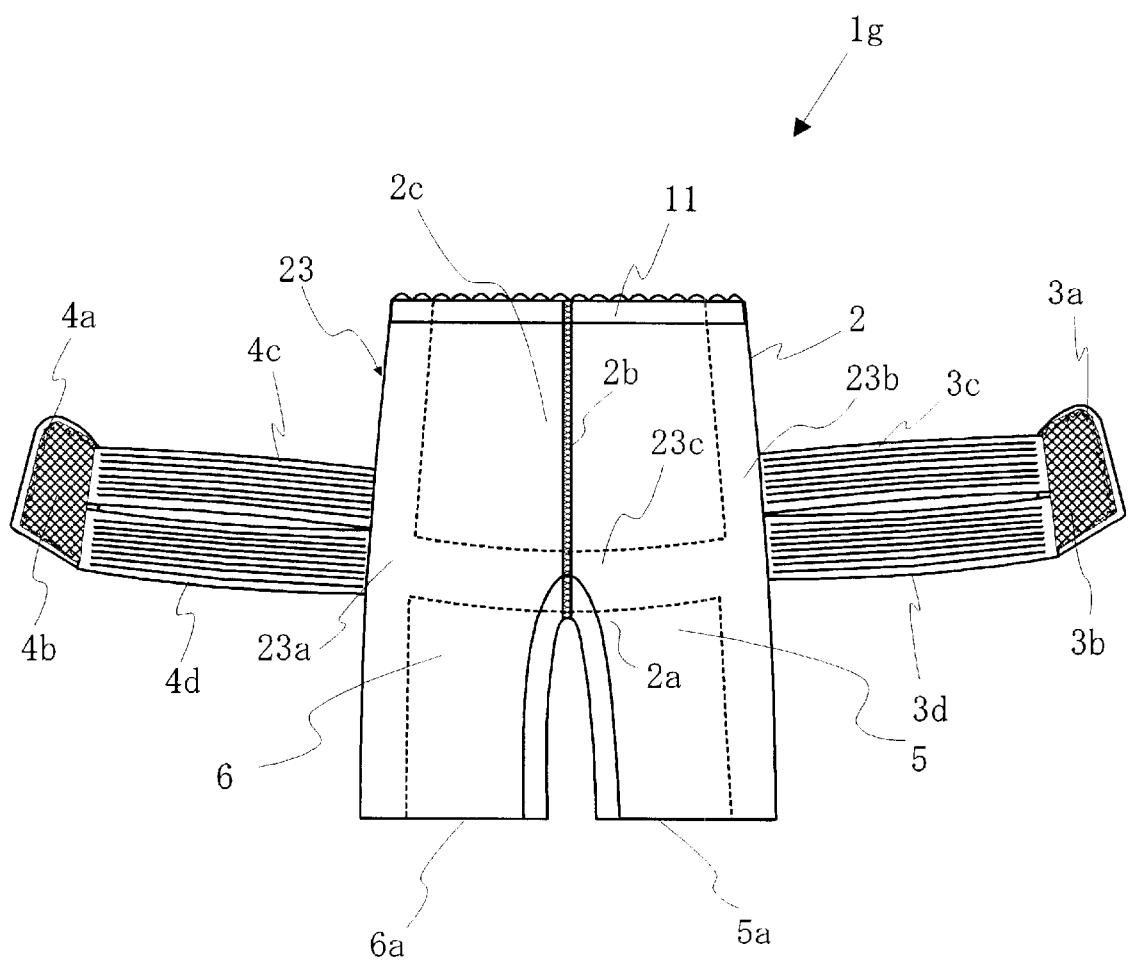
FIG. 19 is a back view showing an eighth embodiment of the lumbago treating girdle according to the present invention before the stretch band is wound therearound.

FIG. 19 is a back view showing an eighth embodiment of the lumbago treating girdle according to the present 6 invention before the stretch band is wound around the girdle. As shown in FIG. 19, in a lumbago treating girdle if of the eighth embodiment, the H-shaped shaping member 23 is sewn onto the back inner surface of the girdle main body 2. The lumbago treating girdle If of the eighth embodiment is constituted by sewing the H-shaped shaping member 23 to the back inner surface of the girdle main body 2 of the lumbago treating girdle 1a of the second embodiment.

Of course, the H-shaped shaping member 23 may be sewn to the back outer surface of the girdle main body 2. The shaping member 23 is constituted of the left vertical piece 23a, right vertical piece 23b and horizontal piece 23c. The horizontal piece 23c is disposed substantially in the middle between the left and right vertical pieces 23a and 23b. In order to sew the shaping member 23 onto the back inner surface of the girdle main body 2, the left vertical piece 23a of the shaping member 23 is sewn onto the left end of the inner surface of the girdle main body 2, the right vertical piece 23b is sewn onto the right end of the inner surface of the girdle main body 2, and the horizontal piece 23c is sewn substantially onto the inner surface of the crotch portion 2a.

The H-shaped shaping member 23 is sewn onto the back inner surface of the girdle main body in this manner. Therefore, when one puts on the lumbago treating girdle 1f of the eighth embodiment, one's lumbar, buttock, femur, and the like can be shaped. The H-shaped shaping member 23 is sewn onto the inner surface of the girdle main body. Therefore, even when one puts on the girdle, appearance is good, and one's lower body can look beautiful. It can be expected that especially women like to use this type of lumbago treating girdle.

The H-shaped shaping member 23 may be sewn onto the lumbago treating girdles 1 to 1e of the first to seventh embodiments.

POSSIBILITY OF INDUSTRIAL UTILIZATION

Since the present invention is constituted as described above, the following effects can be obtained.

First, the present girdle for treatment provides no feeling of pressure because of the V-shaped seam and inverse-triangular press portion disposed on the main body.

Secondly, one or two wide left and right stretch bands of the present lumbago treating girdle are crossed at the buttock part and attached to the vicinity of the femoral parts of the front surface, or the stretch bands can be attached to the back surface in the X shape or the horizontal shape so that the stretch bands can finely be adjusted. Therefore, a balance between left and right pelvis parts is enhanced, gluteus maximum muscle is strengthened, comprehensive medicine including prevention, cure and rehabilitation is performed on the entire lumbar, and lumbago can be treated and completely cured in a relative short term.

Thirdly, in the present lumbago treating girdle, an outer periphery of upper and lower engaging members is sewn to form the middle overlapped portion. Therefore, men can quickly and easily open the girdle during urination.

Fourthly, since push-up materials having no stretching properties are sewn into the left and right side surfaces, front middle surface, and back middle surface of the present lumbago treating girdle, there can be provided the lumbago treating girdle functionally superior in a beauty effect that one's lower body looks remarkably beautiful.

What is claimed is:

1. A lumbago treating girdle comprising: a girdle main body including an inverse-triangular press portion provided with a zipper extending in a vertical direction to a crotch portion from a belt disposed on an upper part of a front surface the girdle main body, a portion sewn in a vertical direction on a back surface of the girdle main body, a right femoral part, a left femoral part, a left engaging member disposed on a left side of said press portion, and a right engaging member disposed on a right side of the press portion; a left stretch band which is attached to a middle of a left end portion of said girdle main body, and to a tip end of which a left engaging member with an engaging piece attached to one surface thereof is attached; and a right stretch band which is attached to a middle of a right end portion of said girdle main body, and to a tip end of which a right engaging member with an engaging piece attached to one surface thereof is attached, said left stretch band being attached to the girdle main body in such a manner that the left stretch band ascends toward the left, and said right stretch band being attached to the girdle main body in such a manner that the right stretch band ascends toward the right.

2. The lumbago treating girdle according to claim 1 wherein the left stretch band comprises an upper left stretch band and a lower left stretch band, and the right stretch band comprises an upper right stretch band and a lower right stretch band.

3. The lumbago treating girdle according to claim 1 or 2 wherein an opening/closing portion is disposed right above the crotch portion.

4. The lumbago treating girdle according to claim 1 or 2 wherein a cross band portion is disposed above the crotch portion.

5. The lumbago treating girdle according to claim 1 or 2 wherein a horizontal band portion is disposed above the crotch portion.

6. The lumbago treating girdle according to claim 1 or 2 wherein a shaping member is sewn onto a back inner surface of the girdle main body.

* * * * *